US00PP22624P2

(12) United States Plant Patent
Ingvoldstad

(10) Patent No.: US PP22,624 P2
(45) Date of Patent: Apr. 3, 2012

(54) ***BEGONIA* PLANT NAMED 'BBEWH12-0'**

(50) Latin Name: *Begonia×tuberhybrida*
Varietal Denomination: BBEWH12-0

(76) Inventor: Ola Ingvoldstad, Brummundal (NO)

( * ) Notice: Subject to any disclaimer, the term of this patent is extended or adjusted under 35 U.S.C. 154(b) by 0 days.

(21) Appl. No.: 12/925,189

(22) Filed: Oct. 15, 2010

(51) Int. Cl.
*A01H 5/00* (2006.01)

(52) U.S. Cl. ..... Plt./343
(58) Field of Classification Search ..... Plt./343
See application file for complete search history.

*Primary Examiner* — Annette Para
(74) *Attorney, Agent, or Firm* — Cassandra Bright

(57) ABSTRACT

A new and distinct *Begonia×tuberhybrida* cultivar named 'BBEWH12-0' is disclosed, characterized by an abundance of outwardly facing, semi double white flowers, bright green, glossy foliage and a short period to begin flowering. The new variety is a *Begonia,* and is normally used as an ornamental garden or container plant.

2 Drawing Sheets

Latin name of the genus and species: *Begonia×tuberhybrida.*

Variety denomination: 'BBEWH12-0'.

BACKGROUND OF THE INVENTION

The new cultivar is a product of a chance discovery. The new variety originated as a chance, whole plant mutation from the, unpatented, variety *Begonia×tuberhybrida* 'Karels Jomfru Rød' The new variety was discovered by the inventor, Ola Ingvoldstad, a citizen of Norway, at a research greenhouse in Brummendal, Norway during 2008, among a planting of the parent variety.

Asexual reproduction of the new cultivar 'BBEWH12-0' was first performed in Norway in 2009. 'BBEWH12-0' has since produced several generations by vegetative cuttings and has shown that the unique features of this cultivar are stable and reproduced true to type.

SUMMARY OF THE INVENTION

The cultivar 'BBEWH12-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BBEWH12-0.' These characteristics in combination distinguish 'BBEWH12-0' as a new and distinct *Begonia×tuberhybrida* cultivar:

1. Abundance of semi-double white flowers
2. Bright, glossy green foliage
3. Short period for plants to begin flowering
4. Flexible plant stems, resisting breakage.
5. Outwardly facing flowers.
6. Many lateral branches per plant.

PARENT COMPARISON

Plants of the new cultivar 'BBEWH12-0' are similar to plants of the parent variety, *Begonia×tuberhybrida* 'Karels Jomfru Rød' in most horticultural characteristics. However, plants of the new cultivar 'BBEWH12-0' produce semi-double flowers, compared to fully double flowers. Additionally, the new variety flowers one week sooner from a rooted cutting than the parent, and produces a white flower, compared to a red flower.

COMMERCIAL COMPARISON

Plants of the new cultivar 'BBEWH12-0' are similar to plants of the unpatented commercial variety, *Begonia×tuberhybrida* 'White Multiflora' in most horticultural characteristics. However, plants of the new cultivar 'BBEWH12-0' produce more flexible branches, brighter green glossier foliage and more flowers per plant. The new cultivar also produces more lateral branches than the comparator.

Plants of the new cultivar 'BBEWH12-0' are similar to plants of the unpatented commercial variety, *Begonia×tuberhybrida* 'Chanson White' in most horticultural characteristics. However, plants of the new cultivar 'BBEWH12-0' produce more flexible branches, brighter green, glossier foliage and more flowers per plant.

BRIEF DESCRIPTION OF THE PHOTOGRAPH

Figure 1:
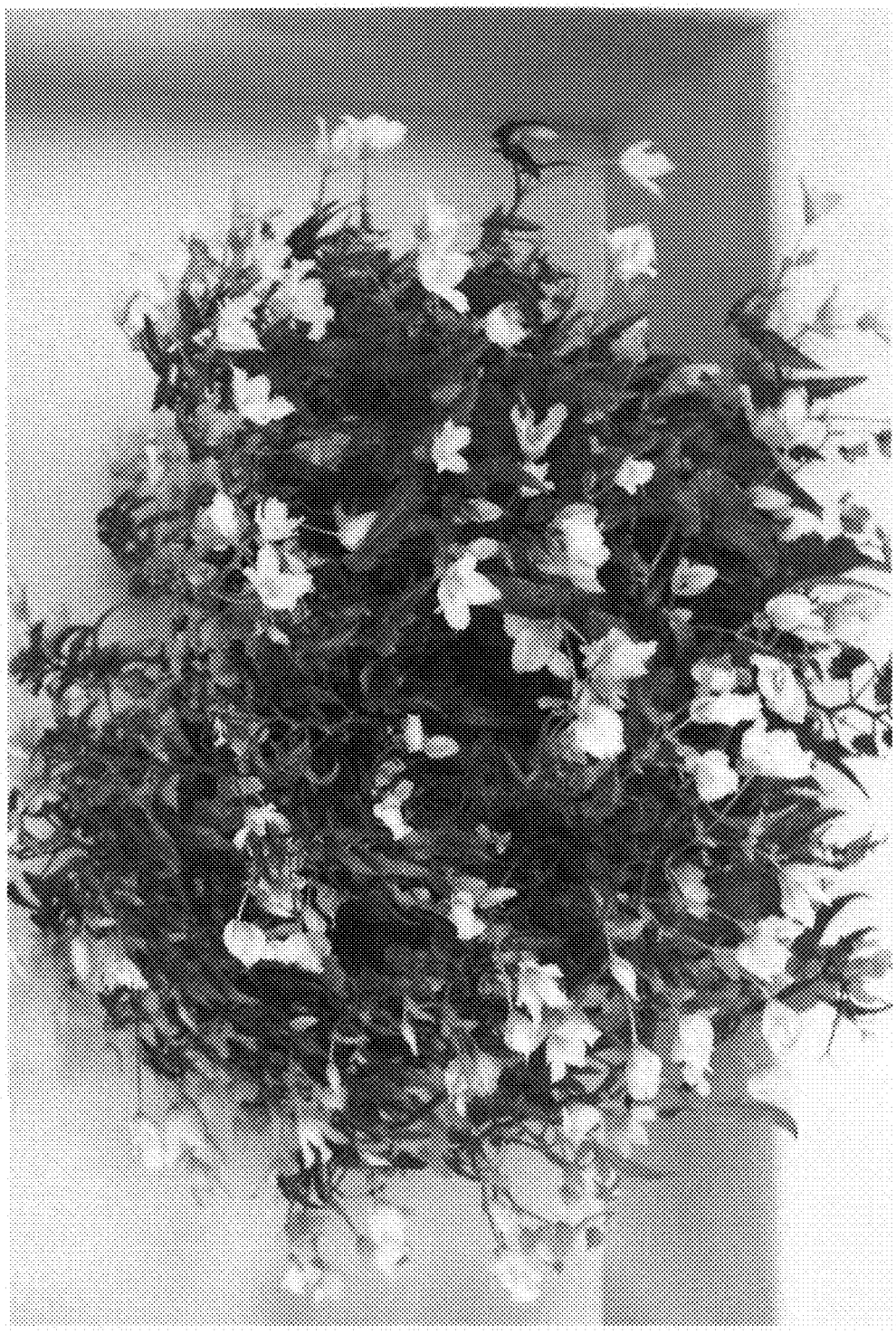

The accompanying photograph in FIG. 1 illustrates in full color a typical plant of 'BBEWH12-0' grown in a greenhouse. The pot size is a commercial 10 inch basket. The plant shown is approximately 9 months old.

Figure 2:
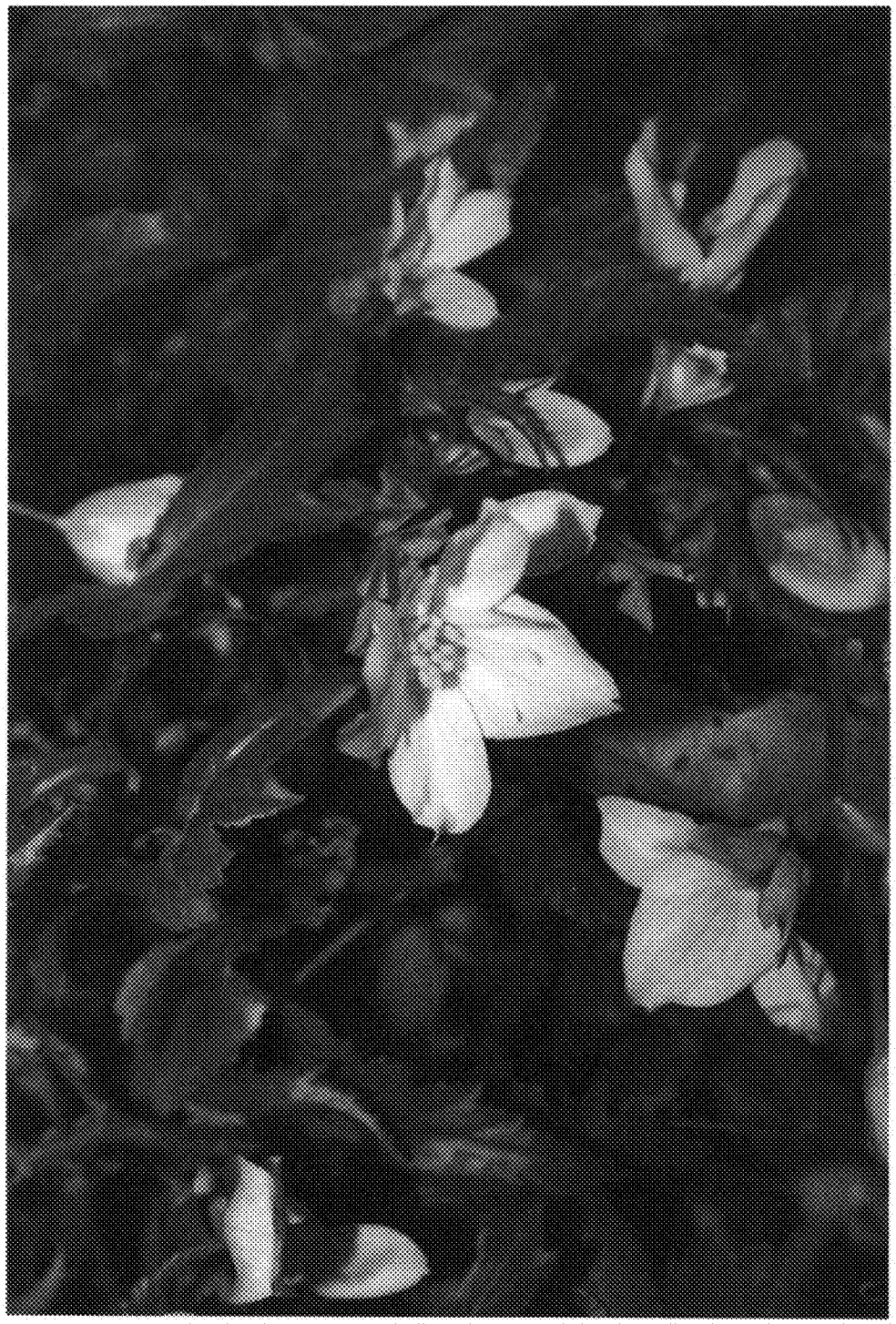

FIG. 2 illustrates a close-up view of the flowers and foliage. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'BBEWH12-0' plants grown in a commercial controlled greenhouse in Oxnard, Calif. Temperatures ranged from 15° C. to 28° C. during the day and 18° C. to 22° C. at night No artificial light, photoperiodic treatments or chemical treatments were given to the plants. Measurements and numerical values represent averages of typical plant types.

Botanical classification: *Begonia×tuberhybrida* 'BBEWH12-0'

Age of plant described: Approximately 9 months.

Container size of plant described: 10 inch basket.

PROPAGATION

Type of propagation typically used: Vegetative cuttings.

Time to roots: About 20 days at approximately 20° C.

Time to produce a rooted cutting/liner: About 30 to 35 days at approximately 20-22° C.

Root description: Moderately dense, moderately branched, fine, fibrous, not fleshy, colored near RHS Grey 201C

PLANT

Growth habit: Mounding, fleshy annual.

Pot size of plant described: 10 inch.

Height: Approximately 26 cm.

Plant spread: Approximately 80 cm.

Growth rate: Rapid.

Branching characteristics: Free branching with numerous lateral branches occurring from multiple basal branches.

Length of primary lateral branches: Approximately 15 cm.

Quantity of primary lateral branches: More than 50

Characteristics of primary lateral branches:

*Form.*—Round in cross section.

*Diameter.*—Approximately 0.5 cm.

*Color.*—Near RHS Yellow-Green 152B, flushed with Red 53B.

*Texture.*—Glabrous, shiny.

*Strength.*—Moderately strong, fleshy, non-brittle.

*Internode length.*—Approximately 1.0 cm on average.

FOLIAGE

*Orientation.*—Outwardly facing foliage. Approximately 75° peduncle angle from stem. Curved peduncle.

*Strength.*—Very strong, resists breakage.

*Texture.*—Smooth, glabrous.

*Appearance.*—Glossy.

*Arrangement.*—Alternate.

*Quantity.*—Approximately 10 per primary lateral branch.

*Average length.*—Approximately 9 cm.

*Average width.*—Approximately 3.3 cm.

*Shape of blade.*—Reniform.

*Apex.*—Acute.

*Base.*—Cordate, asymmetrical.

*Margin.*—Double serrate.

*Texture of top surface.*—Glabrous.

*Texture of lower surface.*—Glabrous.

*Pubescence.*—None.

*Aspect.*—Recurved.

*Color.*—Young foliage upper side: Near RHS Green 137B. Margin near Red-Purple 59C. Young foliage under side: Near RHS Green 138C with margin near Red-Purple 59C. Mature foliage upper side: Near RHS Green 137A. Mature foliage under side: Near RHS Green 138B.

*Venation.*—Type: Palmate. Venation color upper side: Near RHS Yellow-Green N144B. Venation color under side: Near RHS Green 138B.

*Petiole.*—Length: Average Range Approximately 2.3 to 3.4 cm. Diameter: Approximately 0.3 cm. Color: Near RHS Greyed-Red 179C. Texture: Pubescent.

*Stipule description.*—Irregularly present, occurring in 1 or 2 per node, non-fleshy, transparent, becoming completely papery before leaves fully expand. Length: Approximately 0.4 cm. Diameter: Approximately 0.3 cm. Color: Near RHS Yellow-Green 145D. Texture: Glabrous.

Flower

Flowering habit: Continuously flowering during Spring and Summer.

Days to flowering from rooted cutting:

Inflorescence and flower type and habit: Single flowers arranged in axillary cymes. Cymes held above foliage, approximately 2 to 3 open flowers per cyme.

Cyme size:

*Diameter.*—Approximately 12 cm.

*Height.*—Approximately 5.0 cm.

Flower longevity on plant: About 10 days.

Persistent or self-cleaning: Self-Cleaning.

Bud:

*Shape.*—Flattened oval.

*Length.*—Approximately 2.1 cm.

*Diameter.*—Approximately 1.8 cm.

*Color.*—Near RHS Green-White 157D with basl flush near Yellow-Green 144C. Overall faintly flushed with Red-Purple 58A.

Flower size:

*Diameter.*—Approximately 5.1 cm.

*Depth.*—Approximately 3.5 cm.

Tepals:

*Quantity.*—Approximately 4 fully expanded, with 2 larger, and 2 slightly smaller. Additionally, 1 to 3 more, highly reduced in size also occurring in mature flowers.

*Arrangement.*—Rosette.

*Length.*—Approximately 3.0 cm.

*Width.*—Approximately 2.0 cm.

*Shape.*—Deltoid.

*Apex.*—Acute.

*Base.*—Truncate.

*Margin.*—Entire.

*Aspect.*—Flat to very slight undulation.

*Texture, upper surfaces.*—Shiny.

*Texture, lower surfaces.*—Matte.

*Color.*—When opening, upper surface: Near RHS Green-White 157D with basal flush near Yellow-Green 144B. When opening, lower surface: Near RHS Green-White 157D with basal flush near Yellow-Green 144B. Fully opened, upper surface: Near RHS White N155B with flush near Red 50B. Fully opened, lower surface: Near RHS White N155B with flush near Red 50B toward margins and apex. Fading to, both sides: Near RHS White N155D with flush near Red 50B toward base.

Flower bracts:

*Quantity.*—2 per cyme, and normally 2 per flower.

*Shape.*—Broad deltoid.

*Length.*—Approximately 0.6 cm.

*Diameter.*—Approximately 0.7 cm.
*Apex.*—Obtuse.
*Margin.*—Entire, slightly dentate near apex.
*Texture.*—Slightly pubescent.
*Aspect.*—Slightly rolled inward.
*Color.*—Near RHS Yellow-Green 144C.

Peduncles:
*Length.*—Average Approximately 2.5 cm.
*Diameter.*—Approximately 0.2 cm.
*Angle.*—About 75° to the lateral branch.
*Strength.*—Moderate, flexible.
*Texture.*—Glabrous, shiny.
*Color.*—Near RHS Greyed-Red 181B.

Pedicels:
*Length.*—Average Approximately 2.2 cm.
*Diameter.*—Approximately 0.1 cm.
*Angle.*—About 15° to the peduncle.
*Strength.*—Moderate, flexible.
*Texture.*—Glabrous, shiny.
*Color.*—Near RHS White N155D with flush near Greyed-Red 181B.

Fragrance: Faint.

REPRODUCTIVE ORGANS

Stamens:
*Number.*—Approximately 20 to 25.

Anthers:
*Description.*—Clublike.
*Length.*—Approximately 0.6 cm.
*Color.*—Near RHS Yellow 9A.
*Pollen.*—Not observed.

Pistil:
*Number.*—1.
*Length.*—Approximately 0.6 cm.
*Style.*—Length: Approximately 0.4 cm. Color: Near RHS Yellow 2B.
*Stigma.*—Shape: Columnar. Color: Near RHS Yellow 3B. Ovary Color: Near RHS Yellow 2D.

OTHER CHARACTERISTICS

Seeds and fruits:
*Fruit.*—Description: Winged capsule. Wing Length: Approximately 1.2 cm. Overall Fruit Length: Approximately 1.5 cm. Overall Fruit Diameter: Approximately 0.9 cm. Color: Near RHS Yellow-Green 144B.
*Seeds.*—Not observed to date.

Disease/pest resistance: Neither resistance nor susceptibility to diseases or pests has been observed in this variety.

Temperature tolerance: The new variety tolerates temperatures from approximately 5° to 25° C.

What is claimed is:

1. A new and distinct cultivar of *Begonia* plant named 'BBEWH12-0' as herein illustrated and described.

* * * * *